United States Patent [19]
Long et al.

[11] Patent Number: 5,276,693
[45] Date of Patent: Jan. 4, 1994

[54] LIGHT-UTILIZING DEVICE INCLUDING A REGION HAVING A NON-ABRUPTLY VARYING REFRACTION INDEX AND A METHOD FOR PRODUCING THE REGION

[75] Inventors: Gary Long, Cincinnati; Arnold H. Deutchman, Columbus, both of Ohio

[73] Assignee: Laser Centers of America, Cincinnati, Ohio

[21] Appl. No.: 944,384

[22] Filed: Sep. 14, 1992

Related U.S. Application Data

[63] Continuation-in-part of Ser. No. 724,019, Jul. 1, 1991, Pat. No. 5,164,945.

[51] Int. Cl.⁵ .............................................. H01S 3/30
[52] U.S. Cl. .................................. 372/6; 385/15; 385/31; 385/39; 385/49; 606/37
[58] Field of Search .............. 372/6; 385/15, 31, 39, 385/49; 128/303.1

[56]     References Cited
        U.S. PATENT DOCUMENTS

| | | | |
|---|---|---|---|
| 4,126,136 | 11/1978 | Auth et al. | 128/303.1 |
| 4,627,435 | 12/1986 | Hoskin | 128/303.1 |
| 4,693,244 | 9/1987 | Daikuzono | 128/303.1 |
| 4,736,743 | 4/1988 | Daikuzono | 128/4 |
| 4,773,413 | 9/1988 | Hussein et al. | 128/303.1 |
| 4,832,979 | 5/1989 | Hoshino | 427/38 |
| 4,878,725 | 11/1989 | Hessel et al. | 385/15 |
| 4,992,298 | 2/1991 | Deutchman et al. | 427/38 |
| 4,994,060 | 2/1991 | Rink et al. | 606/28 |

OTHER PUBLICATIONS

Informational material entitled "Ion Implantation (Advanced Technologies for Surface Engineering)", from BeamAlloy Corporation of Dublin, Ohio, 1989.
Informational literature entitled "Surface Engineering-R and D Services," from BeamAlloy Corporation of Dublin, Ohio.
Article entitled "Ion Nitriding and Nitrogen Ion Implantation: Process Characteristics and Comparisons", by Deutchman et al., Industrial Heating, Jan. 1990, pp. 32-35.
Article entitled "Practical Applications of Ion Beam Mixing: A New Surface Technique", by Deutchman et al., Industrial Heating, Feb. 1988, pp. 30 and 31.
Article entitled "Deposition-A Gem of a Process", by Deutchman et al., Advanced Materials and Processes Jun. 1989, pp. 29-33.
Article entitled "Application and Utility of Industrial Diamond-Like Films", by Deutchman et al., Industrial Heatng, Jul. 1988, pp. 12-14.
Article entitled "Graded-Index Surfaces and Films", by W. H. Lowdermilk and D. Milam, handbook of Laser Science and Technology, 1981.

*Primary Examiner*—Georgia Y. Epps
*Attorney, Agent, or Firm*—Lowe, Price, LeBlanc & Becker

[57]          ABSTRACT

A thin layer of a material having a refractive index that varies non-abruptly between the refractive indexes of a first element and a second element in an optical device significantly reduces Fresnel losses in transmitting light from the first element into the second element. The layer is readily created by either an ion beam mixing process or by an ion beam enhanced deposition (IBED) process, forming a region of non-abruptly varying refractive index in one of the elements at an interface therebetween. A selected material is thus securely bonded into the laser light-receiving element which may conveniently be made of a material such as YAG, silica, sapphire, zirconia, quartz, silicon, germanium, zinc sulfide or zinc selenide, depending on the application at hand. In another aspect of this invention, the tip element is provided with an additional layer over the first layer to provide added protection thereto.

40 Claims, 4 Drawing Sheets

LIGHT-UTILIZING DEVICE INCLUDING A REGION HAVING A NON-ABRUPTLY VARYING REFRACTION INDEX AND A METHOD FOR PRODUCING THE REGION

This is a continuation-in-part of copending application U.S. Ser. No. 07/724,019, filed on Jul. 1, 1991, U.S. Pat. No. 5,164,945.

FIELD OF THE INVENTION

This invention relates generally to a device receiving and efficiently transmitting or utilizing light and more particularly to a light-utilizing device having an optical element which includes a region having a non-abruptly varying refractive index to facilitate transmission of received light, to facilitate absorption of a selected portion of received light, or to reduce reflection at a light receiving surface region, and to methods for producing such regions.

BACKGROUND OF THE PRIOR ART

There are numerous devices which include optical elements in which light is received or through which light is transmitted. If the received light is to be transmitted through the optical element, it is desirable to reduce Fresnel losses caused by abrupt changes in the index of refraction, e.g., when light travelling through a vacuum or air reaches the optical element.

It has long been known to provide surface layers to such optical elements, wherein the index of refraction can be varied controllably to provide antireflection properties. Such antireflection layers are typically provided at the surfaces of a variety of optical elements, and often such layers are absolutely necessary for optimum performance of the devices. The optical elements themselves may be very small, e.g., the end of an optic fiber, or may be comparatively large, for example a canopy of a high performance fighter aircraft at which radar reflections are to be reduced.

The copending application on which this continuation-in-part is based, U.S. Ser. No. 07/724,019 U.S. Pat. No. 5,164,945 deals principally with laser devices, such as contact surgical devices in which laser light is applied as a laser light flux of intense energy for ablation or vaporization of tissues. Such devices typically include a tip formed of a ceramic material, e.g., YAG, sapphire, zirconia or silica, to which laser light is provided through an optic fiber having a different index of refraction. The parent application focused principally on methods and optical structures for obtaining reduced Fresnel losses at interfaces between two elements through both of which the laser light was to be transmitted efficiently. In such applications, Fresnel reflections tend to create an undesirable hot zone near the interface where the refractive index changes abruptly. In the prior art, this was typically dealt with by cooling of the interface region. Such a solution requires additional elements in the laser optical system and tends to make the surgical tool bulky and unwieldy.

There are many other situations were Fresnel losses produce other kinds of problems.

As is well-known, the display screens of computer monitors often produce a glare when viewed in ambient fluorescent or incandescent light because of reflection from the screen to the eyes of the operator. This is typically true both for cathode ray tube-type display devices and for liquid crystal-type and plasma discharge-type devices.

Numerous filter-type elements have been designed and are marketed for placement over a visible portion of the device being observed by a user to reduce such glare. These filter-type screens work by attenuating the reflected light by passing the reflected portion of incident ambient light through a polarizing filter or a tinted (baned pass) filter. Unfortunately, light emitted from the displayed device itself is also thus attenuated, thereby reducing the visible intensity and readability of information displayed on the device screen. Such filter devices are often cumbersome and can easily become dislodged from the display screen.

Incorporating an antireflection layer in the outer surface of the display screen glass itself should provide a major improvement in the overall visual appearance of the output of the display. A graded refraction index layer, with a very narrow band rejection filter, can be designed and formed in the output surface of the display screen, to attenuate only that portion of the optical spectrum which produces the undesirable reflected glare. If this is done, the light produced by the display screen itself will not be attenuated, thereby producing an output image which is perceived to be brighter. This, when coupled with a reduction in reflected glare from the surface of the screen due to ambient lighting will produce an output image which is brighter and clearer and will therefore be easier for an operator to read. With the increasing concern nowadays over job-related stress and trauma, such a solution to reduce operator fatigue is obviously desirable.

As noted earlier, canopies of hard performance fighter aircraft also require that antireflection layers be applied to both the inside and outside surfaces. On the inside surface of the canopy, antireflection coatings are desirable to reduce glare caused by internal lighting, to facilitate observation of the flight instruments and indicators by the occupants of the fighter aircraft. The outside layer is also preferably formed to allow reduced reflection, so as to function both as a radio wave absorber (for reduction of the radar cross-section of the aircraft) and as an optical light transmitter (to enhance visibility of the outside to the plane's occupants). Considering the size and shape of the typical fighter aircraft canopy, the needed antireflection surface properties coatings and band pass filters are difficult to manufacture with known antireflection coating techniques.

Another class of optical devices requires that received light, which may be within a relatively broad range of wavelengths, be readily passed within a selected band of the received optical spectrum while being minimized in other selected bands of the same received spectrum. For such optical devices, it is desirable to be able to provide an antireflection band pass filter in the light-receiving surface of the optical element. An example of such an optical device is an infrared sensing detector which usually is fabricated from materials such as cadmium sulfide and mercury cadmium telluride, which are materials sensitive to infrared radiation in the 0.5 to 20 $\mu$m wavelength range. These infrared sensors are found in a variety of infrared sensing/imaging devices, such as the sensors for heat-seeking missiles, wind shear detectors for aircraft, and infrared imaging satellites. The infrared-sensitive detector materials must be protected from the environment and are thus always placed behind protective windows and focusing lenses. These windows and lenses must be fabricated from infrared-transmitting materials which typically include quartz (silicon-dioxide), silicon, germanium, zinc sulfide and zinc selenide. The specific material is selected to ensure that only a selected portion of the received infrared spectrum is detected or imaged.

In all such devices, however, the index of refraction of the materials of the optical device is higher than that of ambient air. This necessitates the use of an antireflection layer to optimize transmission of the selected band of the infrared radiation which is to be detected or imaged through the protective window or lens. In many cases, conventionally deposited antireflection materials, such as magnesium fluoride or silicon monoxide, do not adhere well to the surface of the infrared window or lens.

The *Handbook of Laser Science and Technology*, at Chapter 2.2, pgs. 431-458, "GRADED-INDEX SURFACES AND FILMS", by W. Howard Lowdermilk et al, discusses a variety of known techniques for providing graded refractive index layers at or on optical substrates and provides an analysis of the physics involved. This reference mentions that graded-index surfaces and films for broad band antireflective (AR) property have important applications in solar energy collection systems, antiglare display cases, and for optical recording discs on which a laser recording is to be made. The reference discusses how to generate and study non-absorbing graded surfaces and films for visible and near-IR light to increase its transmission through a substrate material. The reference states that such an antireflective treatment is typically obtained by chemical leaching and etching of a light-receiving surface of an optical substrate to remove certain components of the substrate material to create a porous, skeletonized, surface region which has pores of a dimension smaller than the wavelength of the light that is to be transmitted. Consequently, such techniques are limited to optical substrate materials with leachable components. Lowdermilk et al also discusses alternatives, including one in which a non-crystalline multicomponent, inorganic oxide film is deposited by a so-called sol-gel process, the film then being itself etched by chemical leaching and/or etching. Another alternative discussed is ion implantation into plastic surfaces, with subsequent etching of the ion tracks to produce a microporous surface region. Yet another proposed alternative is to form a so-called "Moth's Eye" type surface which has distributed fine protuberances on a light-receiving portion thereof. The last alternative discussed by Lowdermilk, at p. 454, is to provide an antireflection coating by adding a surface layer and then applying a laser to generate therefrom a laser-induced damage of the coating layer.

As will be readily perceived, leaching, etching, applying an added-on layer (which itself may thereafter by leached or etched), and other variations of such known techniques, all have significant limitations. Such limitations relate not only to the choice of materials, problems associated with producing very small or very large uniformly graded refraction index regions, high cost, and the risk that for precisely dimensioned elements such as optical lenses there will be a deleterious effect on the focusing capability of the optical element and hence of a more complex device utilizing such an optical element.

There is, therefore, a clear need for optical elements which have a region of non-abruptly index of refraction to minimize losses when light is received or to facilitate absorption or transmission of selected wavelengths of the received light, and for methods which enable this to be realized without physically damaging the light receiving surface and which do not significantly alter the geometry of the surface itself.

The present invention specifically addresses these needs, and is described fully with reference to drawing figures illustrating exemplary structures and geometries. It should be appreciated that the following description is not intended to be limiting, and it is expected that persons of ordinary skill in the art upon reading and understanding this invention will be led to make obvious modifications thereto for specific applications.

As previously noted, the parent application focused principally on the transmission of laser light into and through optical elements in a system utilizing laser light. It is specifically noted that, other than the fact that the structural forms and methods discussed therein pertained principally to uses of laser light for surgical applications, they are readily adaptable to light of any selected wavelength or combinations thereof. In other words, while laser light is coherent light, unlike light comprising a relatively wide range of wavelengths, the basic solution of providing a region of non-abruptly varying refraction index at a selected surface of an optical substrate or device is the same as in the parent application. For this reason, the teaching of the parent application, insofar as it is relevant in these regards, is expressly incorporated herein by reference.

SUMMARY OF THE DISCLOSURE

A principal object of the present invention is to provide means by which light passing through a region or element having a first index of refraction passes into a treated light-receiving surface of another element with very low Fresnel losses at an interface therebetween.

Another object of this invention is to provide a region of non-abrupting varying refractive index to an optical substrate to facilitate transmission therethrough of received light within a predetermined range of wavelengths.

Another related further object of this invention is to provide a region of non-abrupting varying index of refraction to an optical substrate to reduce reflection of light within a selected range of wavelengths incident thereon.

Another related object of this invention is to provide an efficient optical device for directed emission of light from a light-delivering end of an optical element.

It is an even further related object of this invention to provide a treatment for a light-receiving, or a light-delivering surface of an optical element to reduce Fresnel losses thereat.

It is yet another object of this invention to provide a method for reducing Fresnel losses due to light-transmission across an interface between two light-transmitting regions having different indexes of refraction.

These and other objects of the present invention are realized by enabling efficient transmission of light conveyed from a light source through a region formed of a first material having a first refractive index into a light-receiving second element formed of a second material having a second refractive index, by providing a layer, formed at either a light-delivering end of the first region or element, or a light-receiving surface of the second element, the layer comprising a third material which has a non-abruptly varying refractive index which is graded between the magnitudes of the first and second refractive indices.

In another aspect of this invention, there is provided an improved method for reducing Fresnel losses when light is transmitted from a first region or element having a first refractive index into a light-receiving second element formed of a second material having a second refractive index, wherein the improvement comprises the provision of a layer formed at one of the light-transmitting portion of the first region or element and a light-receiving surface of the second element, the layer comprising a third material having a non-abruptly varying refractive index which is graded between the magnitudes of the first and second refractive indexes.

DESCRIPTION OF THE PREFERRED EMBODIMENTS

Light is merely electromagnetic energy in the form of a radiation, which is often characterized by its wavelength as x-ray, ultraviolet, visible, infrared or radio energy. Laser light is only one form of light that has desirable attributes for certain purposes. For present purposes, it should be regarded only as an example of "light".

It is believed that the requirement that the best mode of the invention be described and illustrated fully is therefore fully met by a detailed discussion of an exemplary laser surgical device which was the principal focus of the parent application. As repeatedly noted above, however, laser light is merely coherent light of a selected wavelength, whereas most light transmission, whether ultraviolet, optically visible, or infrared, tend to include electromagnetic radiation within a predetermined range of wavelengths.

The solution provided by the present invention, in principle is exactly the same whether the optical device utilizes laser light or light which includes electromagnetic radiation within a band of wavelengths. The only significant difference will be in the selection of the material or materials utilized to create the region of non-abruptly varying refraction index. Persons of ordinary skill in the art can be expected to select the materials, to generate the necessary ions therefrom, and to apply the materials, as disclosed herein, without undue experimentation, to serve their specific needs according to the disclosed invention.

Accordingly, the detailed description which follows relates initially to an exemplary laser utilizing device but is not intended to be limited thereto. Other applications to utilize ultraviolet, visible spectrum, infrared and radio frequency radiations are also described below.

A surgeon employing laser energy for surgical purposes typically holds in his hand a lightweight handpiece (not shown) into which fits an elongate assembly having a tip element emitting laser light energy for cutting, cauterizing and/or coagulating tissue on which he is operating. As best understood with reference to FIG. 2, such a hand-held assembly 100 has a slim, elongate body 102 connected to a flexible element 104 at a junction 106. The flexible element 104 comprises an outer tubular sheath protectively containing a suitable length of an optic fiber connected by a junction 108 at one end to a source of laser energy (not shown). Laser light energy of a suitable wavelength is received at junction 108 from a laser source located at a distance from the patient and is conveyed by internal reflection within the optic fiber to be delivered through a delivery end 200 of hand-held element 100.

Figure 1:
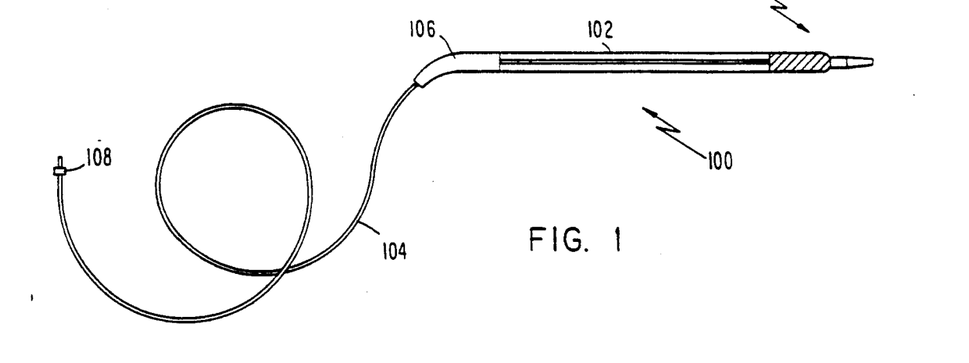
FIG. 1 schematically illustrates elements of an exemplary apparatus by which light received from a laser energy source is conveyed to a laser light emitting tip for surgical procedures.
Figure 2:
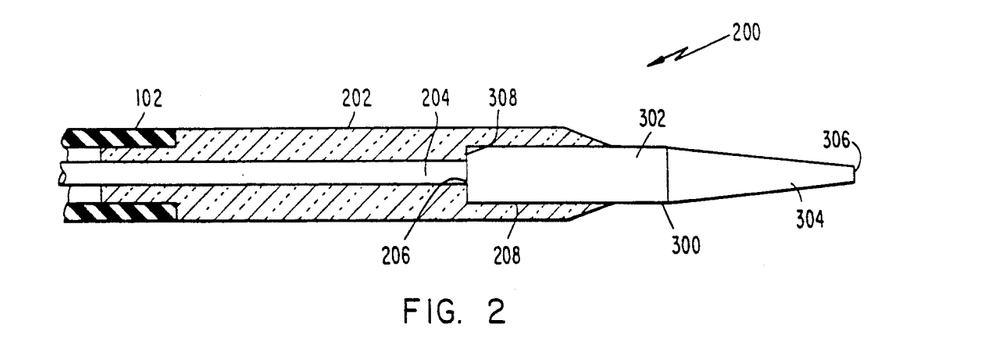
FIG. 2 is a partially-sectioned enlarged view illustrating details at the tip end of the apparatus of FIG. 1.

As illustrated in FIG. 2, delivery end 200 of the device at a forward end of elongate element 102 is connected in known fashion to a fiber/tip connector 202 which is preferably made of stainless steel or other readily sterilizable material. An optic fiber 204 is passed into fiber/tip connector 202 so that laser light energy conveyed by internal reflection through optic fiber 204 is deliverable through an end face 206. The fiber/tip connector 202 is formed with a cylindrical recess 208 at its forward end. Received therein is one end of a tip element 300, to receive laser light energy from optic cable 204.

Figure 3A:
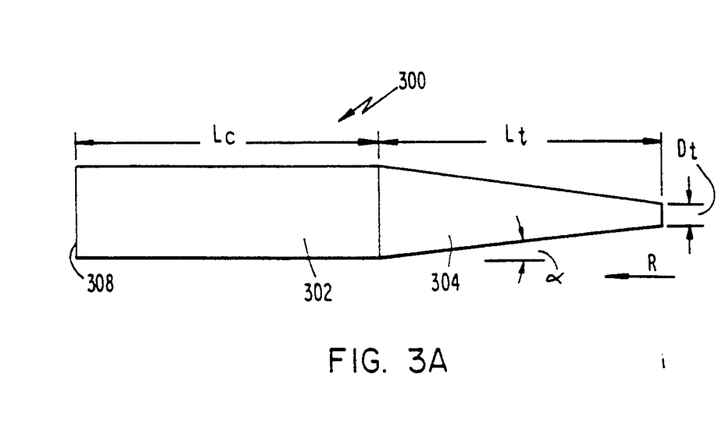
FIGS. 3A and 3B are, respectively, a side view and an end view (in the direction of arrow R) of a conveniently shaped laser light emitting tip element.
Figure 3B:
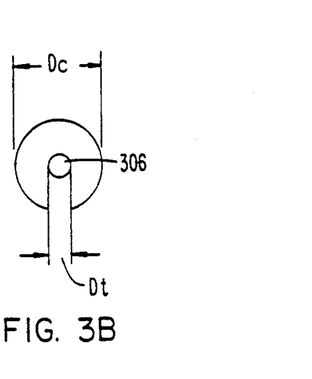

Referring now to FIGS. 3A and 3B, tip element 300, according to a preferred embodiment of the present invention, has a cylindrical portion 302 of length "$L_c$" and a coaxially tapered portion 304 of length "$L_t$" which ends at its smallest cross-section portion at a laser light delivery end surface 306. At the other end of tip element 300 is a laser light receiving surface 308 which is typically epoxied directly to the laser light delivery end surface 206 of optic fiber 204 with a clear epoxy glue, e.g., EPO-TEK 301-2.

As illustrated in FIG. 3B, the maximum diameter of tip element 300 is "$D_c$" and the minimum diameter, at the laser light delivery end surface 306 is "$D_t$". The external surface of tapered portion 304 is conical in shape and is inclined at an angle "$\alpha$" with respect to the cylindrical surface of portion 302. "α" preferably is between 6° and 15°.

Other shapes, e.g., a right cylinder of circular or other cross-section, or a combination of a cylinder and an end portion with a rounded end, etc., may be employed to suit specific needs as broadly disclosed herein. The detailed discussions of beneficial surface treatments provided at the light receiving and energy delivery end of the tip element therefore have broad applicability, by logical extension of the same inventive principle, regardless of the shape of the tip element body through which laser light energy is transmitted thereafter.

Tip element 300 is preferably made of a clear crystalline material, e.g., a ceramic material such as zirconia YAG, sapphire, zirconia, or silica. Any known techniques may be used to form the selected material into the final shape of tip element 300. It is important, however, that end surfaces 206 and 308 be made smooth and clear to transmit laser light therethrough, i.e., from optic fiber 204 into tip element 300. Also, side surfaces 304 and 306 of tip element 300 are smooth to facilitate internal reflection as well as ion beam mixing or ion beam enhanced deposition of a selected material for laser light absorption thereat according to certain embodiments. The precise lengths and diameters of various portions of tip element 300 may be selected by persons of ordinary skill in the art to suit the specific operational needs to be served by the device, e.g., as a scalpel or a cauterizer.

Relevant properties of the materials of interest are tabulated in Table 1 below.

TABLE 1

|  | Melting Point (°C.) | Thermal Conductivity (W/m °C.) | Refractive Index at 1.06 μm Wavelength |
| --- | --- | --- | --- |
| Sapphire ($Al_2O_3$) | 2300 | 35 | 1.75 |
| Silica ($SiO_2$) | 1740 | 7 | 1.54 |
| YAG ($Y_3Al_5O_{12}$) | 2220 | 13 | 1.82 |
| Zirconia ($Z_rO_2$) | 2690 | 2.1 | 2.13 |

Regardless of the shape and size of tip element 300, the safety of the patient and the convenience of the surgeon both require minimization of energy losses within the device. To avoid the need to cool the interface between optic fiber 204 and cylindrical portion 302 of tip element 300, structure must be provided there to reduce so-called "Fresnel losses". Such losses can, in principle, be reduced by providing a conventional antireflection coating, but this has been found to be inadequate in terms of both reliability and durability.

In principle, the overall area over which light is received, transmitted or absorbed is irrelevant. Thus, it is merely a matter of choice whether laser light is to be transmitted from an optic fiber 204 into tip element 300 or infrared light is to be received from the ambient atmosphere into a detector element window.

Note that optic fiber 204 in the exemplary laser device is bonded at its outside surface to the inside surface of the hole in fiber/tip connector element 202. The refractive index of the epoxy material used for such purposes is typically equal to or greater than that of silica, but is also typically less than that of the material of which the tip element is made. The epoxy must also be transparent to the wavelength(s) of the laser light used. The glass transition temperature of the epoxy preferably should be approximately 200° C. to assure a strong bond even if the connector should become hot during, for example, prolonged use. It is also possible to bond the fiber/tip connector 202 to the tip element 300 with an epoxy material which is not transparent, but is stronger and has a higher glass transition temperature. Suitable epoxy materials are commercially available.

Although the term "optic fiber" is utilized in this discussion, there is no reason why, at least in principle, one cannot utilize a multi-strand optic fiber in place of a monofilament optic fiber 204 as illustrated. Likewise, depending on the application at hand, the physical counterpart of the typical small diameter optic fiber 204 may in fact be larger than the counterpart of the tip element 300. Similarly, materials other than ceramic materials such as YAG, sapphire, zirconia, or silica may be used to form tip element 300 or a much larger and flatter counterpart, e.g., a fighter plane canopy or window, and its shape may be formed by shaping and polishing of an element of the selected material.

Depending on its size and other specific needs, the body of tip element 300 may be molded or grown as a shaped crystal. In any case, the cylindrical, tapered and end surfaces of tip element 300 should be made smooth to facilitate internal reflection and to minimize heating due to laser light absorption thereat except where such absorption is desired and is intentionally provided as described hereinafter.

Material used to form optic fiber 204, e.g., silica, typically have a refractive index in the range 1.4 to 1.55, and materials suitable for forming tip element 300, e.g., ceramic materials such as silica, YAG, sapphire and zirconia typically have refractive indices within the range 1.4 to 2.13. It is thus readily seen that laser light which travels by internal reflection along optic fiber 204 moves from a region of relatively low refractive index and into a region of relatively higher refractive index upon entry into tip element 300. It is believed that it is this sudden change in refractive indices, going from a relatively low refractive index (optic fiber), to a relatively high refractive index material in the tip element (e.g., sapphire), which causes significant local losses (generally referred to as "Fresnel losses") at the fiber/tip interface with undesirable heating thereat.

In the broader context, and regardless of the band of wavelengths characterizing a particular electromagnetic transmission, one may want to hold to a minimum any transmission losses at an interface between two regions or elements of different refractive indexes.

In a preferred embodiment of the present invention, a thin region 310 having a graded refractive index and comprising a varying concentration of suitable material, e.g., silica, of a thickness "t", is provided at the laser light receiving end surface 308 of tip element 300. See FIGS. 4B and 4D. It is important that the material constituting region 310 have a refractive index varying between the respective refractive indices of optic fiber 204 and tip element 300. Ideally, such a region should have a refractive index at its outermost surface 308 equal in magnitude to that of the optic fiber 204 and changing non-abruptly over the thickness "t" to a magnitude equal to that of the material of which the bulk of tip element 300 is formed, e.g., ceramic materials such as YAG or sapphire.

Figure 4A:
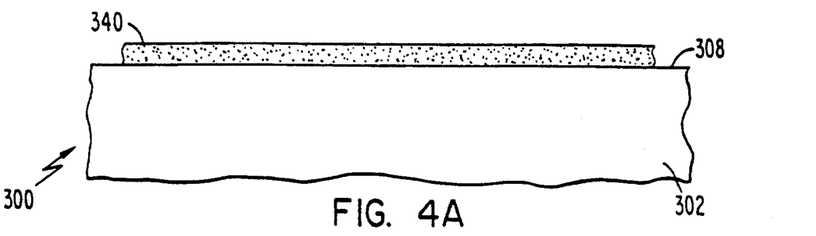
FIGS. 4A and 4B are schematic illustrations depicting stages in the treatment applied at the light-receiving end surface of the tip element by an ion beam mixing process and FIGS. 4C and 4D for an ion beam enhanced deposition process, respectively, to generate a region in which a refractive index is graded between the magnitudes of the refractive indices of the materials of an optic fiber and a tip element.
Figure 4B:
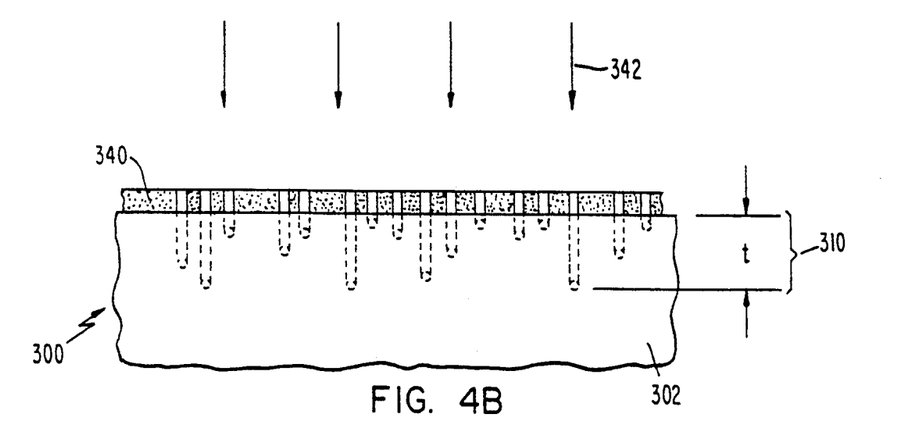
Figure 4C:
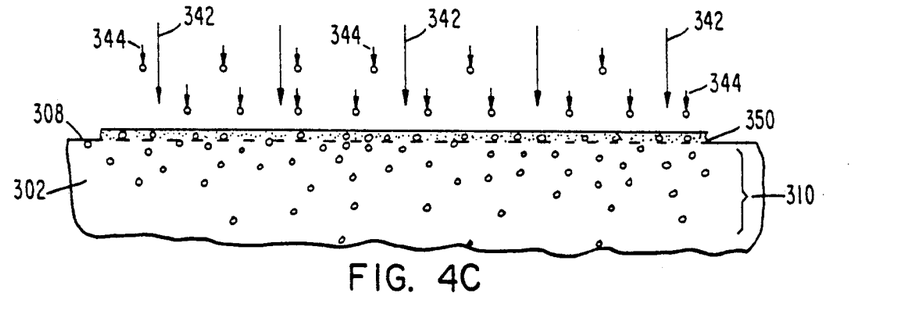
Figure 4D:
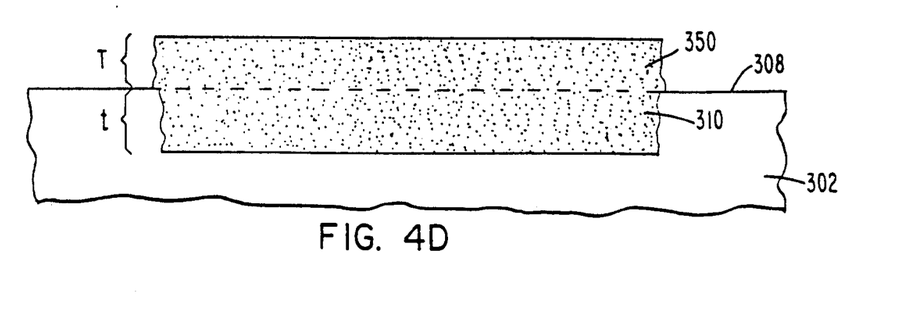
Figure 5A:
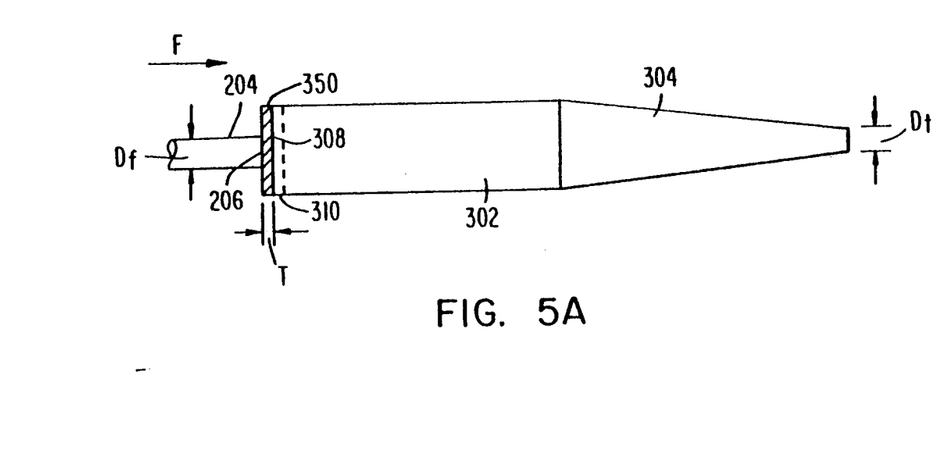
FIGS. 5A and 5B, respectively, are a side view and an end view (in the direction of arrow F) of a light delivering end tip element provided with an intermediate graded refraction index layer and an added layer of silica at a light receiving end according to a preferred embodiment of this invention.
Figure 5B:
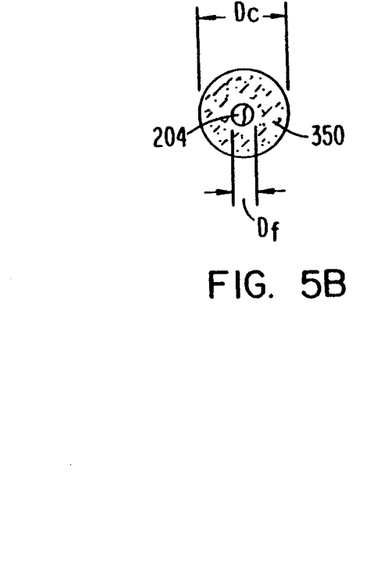

It is found that the incorporation of small amounts of a selected ceramic-type material, such as $SiO_2$ within the material of tip element 300, e.g., ceramic materials such as YAG or sapphire, in the region immediately adjacent the physical end surface 308, creates such a region, illustrated in FIGS. 4B and 4D as a layer 310, of the desired non-abruptly varying refractive index and thickness. This is most conveniently accomplished by either of two processes commercially developed by Beamalloy Corporation, of Dublin, Ohio, and hitherto employed for other advantageous results, e.g., to create a hard surface region. These processes are known in the art as the "ion beam mixing process" and the "ion beam enhanced deposition process", respectively. A suitable thickness for such an intermediate graded refractive index layer 310 is in the range 50 Å to 10,000 Å. Other thickness may be desirably for specific applications, e.g., on the surface of a sensor element that may be exposed to abrasion from ambient wind-carried dust or corrosive pollutants in the ambient atmosphere.

In the "ion beam mixing process" a thin film 340, typically 1000 Å or less in thickness, of a selected material, e.g. silica, is deposited on the light-receiving surface 308 of tip element 300 by any known technique such as sputtering or the like. See FIG. 4A. This film 340 is then subjected to illumination by an ion beam 342 comprising ions of an inert gas such as argon, xenon or krypton, or neon. The energetic impacts of such ions drives the silica from film 340 into the YAG or sapphire material of tip element 300 to a selected depth. See FIG. 4B. With the proper choice of implant parameters, e.g., the film material, its thickness, the ion species and energies (in KeV), and the time for which the ion beam is applied, the entire deposited film can be implanted/-mixed into, i.e., "alloyed" with, the substrate or target material.

Naturally, the concentration of the "implanted" or "mixed-in" material diminishes within the layer or region 310 from the outside surface 308 into the tip element material in a non-abrupt manner. Consequently, the refractive index across the thickness "t" thereof also varies in a non-abrupt manner, changing from that of the film material to that of the tip element material. Thus, if silica is the chosen film material, laser light from a silica optic fiber 204 will not encounter an abrupt change in refractive index and no Fresnel losses will occur as the laser light passed through the varying refractive index layer 310 into the body of tip element 300.

Another very significant advantage is that the layer 310 provided in this manner is alloyed with and remains very much a part of the tip element and will not delaminate or peel away therefrom during subsequent thermal cycling of the tip element in use.

In the "ion beam enhanced deposition process" the provision of selected material, e.g., silica 344, and the ion beam bombardment thereof, both occur simultaneously. This results in a silica layer 350 that is grown on the surface and is continuously and simultaneously modified by the ions energetically driving the silica across the surface 308 into the material of tip element 300 to form a layer 310 having the desired properties, i.e., varying and graded refractive index and no likelihood of delamination. For simplicity and convenience this is schematically illustrated in FIG. 4D, for both the "ion beam mixing process" and the "ion beam enhanced deposition process." U.S. Pat. No. 4,992,298, to Deutchman et al., titled "Dual Ion Beam Alloying Process," describes apparatus and a method for one form of the "ion beam enhanced deposition process" as described herein and is incorporated herein by reference for additional related details disclosed therein.

As will be readily appreciated, if the surface area over which the "ion beam mixing" or the "ion beam enhanced deposition" is to be applied is large, a correspondingly longer time may be required to perform the process. Thus, for example in generating a thin surface region of non-abruptly varying refractive index by either technique on a fighter plane window (to enhance absorption thereat of enemy radar energy) a considerably longer time may be required than in similarly treating a laser surgical tip.

As will be appreciated, such an additional layer may be formed of a material selected for enhanced resistance to abrasion, pollutant/corrosion resistance, or the like.

It may be even more advantageous to apply an additional thin film 350 of silica (or other selected material) of thickness "T" to layer 310 to be contiguous therewith, as illustrated schematically in FIG. 4D. Such an added silica layer 350 will be very securely bonded to the silica-rich surface 308 into which silica has previously been implanted to form the graded refractive index layer 310 of thickness "t".

The additional thin film 350 can, in practice, be added after the "ion beam mixing process" is completed. However, as a matter of production efficiency, this is best accomplished by the "ion beam enhanced deposition process" by simply continuing to deposit silica after reducing the energy level in the ion beam until the desired final thickness of silica layer 350 is obtained. When this is done, the result is a strong secure bond between layer 350 of silica to the varying refractive index layer 310 forming the light-receiving end of tip element 300. See FIG. 4D.

Figure 6A:
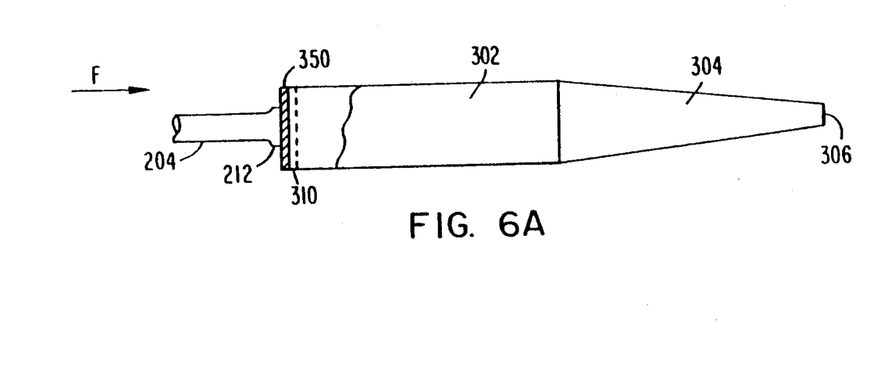
FIGS. 6A and 6B, respectively, are a partially sectioned side view and an end view (in the direction of arrow F) of a third embodiment of the present invention.
Figure 6B:
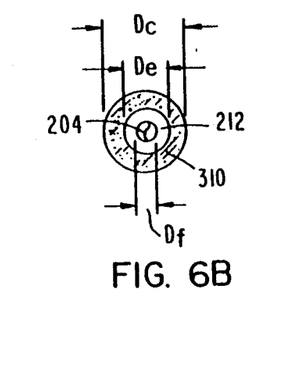

FIGS. 6A and 6B depict yet another embodiment of the present invention. In this variation, the laser light energy delivering end of optic fiber 204 is enlarged, e.g., by localized heating and deformation, so that it has an enlarged diameter end portion 212 which contacts intermediate refractive index layer 310 over a correspondingly larger area. It will be readily seen from FIG. 6B that "$D_e$", the diameter of the enlarged end of optic fiber 204, is larger than the diameter "$D_f$" of the rest of the optic fiber.

In all of the embodiments described hitherto, a controlled flow of laser light is emitted from surface 306 at the forwardmost point of laser tip 300. Typically, such laser light emissions may be utilized to ablate or vaporize material, e.g., body tissues of a patient, immediately in front of surface 306. The rate at which this can be accomplished is determined by the rate at which the energy is provided to the tissue and by whether or not the tissue in question is in direct contact with the surface through which the energy is transmitted into the tissue. For certain applications, e.g., the ablation of diseased dental material of a tooth, actual contact between an energy emitting surface and the tissue to be ablated may not be required or advisable. However, physical contact between an energy providing surface and soft body tissue may be desirable in other applications, e.g., for cauterization. Relatively low laser energy transfers may also be required to cause local heating and coagulation of blood at and around surgical sites.

Figure 7:
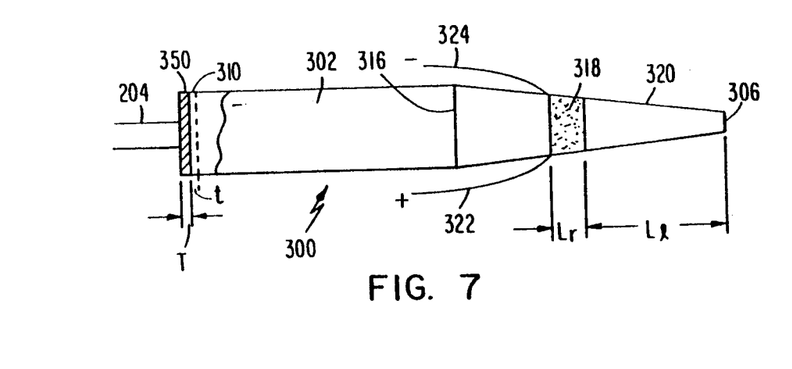
FIG. 7 is a partially sectioned side view of a laser light emitting tip element, generally similar in shape to the embodiment illustrated in FIGS. 5A and 5B, also including an ohmic heating layer provided for controlled ohmic heating at a selected portion of the laser light delivering tip element.

For certain applications, it may be desirable to have a portion of the tip element delivering emitted laser light received therein to perform ablation/vaporization of tissue while, at the same time, providing controlled ancillary local heating at a portion of the tapered surface of the tip element. FIG. 7 depicts a structure of an embodiment suitable for this purpose. In this embodiment, between end face 306 and the peripheral line 316 at which cylindrical portion 302 joins tapered portion 304 there is provided a surface layer 318 of an electrically resistive material deposited in any known manner. For purposes of illustration, the electrically resistive layer 318 is shown in FIG. 7 as having an axial length "$L_r$" with a length "$L_1$" left as an unlayered portion 320 of the tip element 300 extending to the laser light emitting surface 306. Electrical leads 322 and 324 are illustrated only schematically in FIG. 8 and may be formed and disposed in any known manner, with suitable insulation, e.g., a silica layer, provided thereover to avoid generating electrical currents between them through surrounding tissue.

During operation of such a device, the surgeon can selectively provide ablative/evaporative energy flows by emission of laser light energy from surface 306 forwardly of tip element 300. Also, as and when appropriate, by forcible sideways contact between the electrically heated resistive surface 318 and body tissues, he or she can be cauterizing or coagulating tissue at the tapered side of tip element 300. The amount of "ohmic heating" generated in electrical resistive layer 318 is determined by its electrical resistance and by the electrical current passed therethrough under the surgeon's control. Such parameters may be selected to be commensurate with the surgeon's needs.

Figure 8:
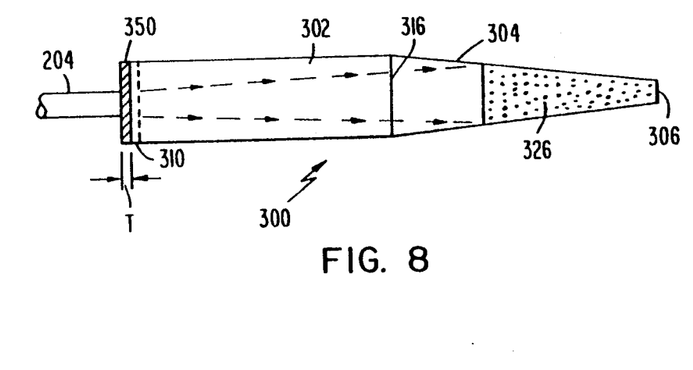
FIG. 8 is a partially sectioned side view of a laser light emitting tip element generally similar in shape to the embodiment illustrated in FIGS. 5A and 5B, provided with a laser light absorbing material on a portion of the tip element.

FIG. 8 depicts yet another embodiment of the laser energy utilizing invention in which, as in all the other embodiments described above, the provision of an intermediate refractive index layer 310 reduces Fresnel losses and efficiently delivers laser light energy to the tapered front end 304 of tip element 300. In this embodiment, an entire end portion of tapered portion 304, including front end surface 306, is provided a coating of a high temperature melting point material such as titanium, chromium, nickel, zirconium, molybdenum, tantalum, tungsten, yttria, zirconia or alumina.

The selected constituent is preferably provided by either one of the ion beam mixing and the ion beam enhanced deposition processes, as previously described, except for the obvious differences in implanted material and related physical parameters, to form a strong metallic/ceramic bonded layer which does not readily detach from the parent material of tip element 300 during prolonged use. With such a structure, laser light energy is emitted from optic fiber 204, passes with minimal Fresnel losses through intermediate refractive index layer 310 into cylindrical portion 302 and then into tapered portion 304. There is, inevitably, some spreading of the beam of laser light in its transmission through cylindrical portion 302 and an adjacent first part of tapered portion 304, as indicated in FIG. 9 by the arrowed broken lines. With knowledge of the various geometric dimensions of tip element 300 and the refractive index of the material forming the same, it should be easy for a person of ordinary skill in the art to compute where the beam of diverging laser light within tip element 300 will be incident at the tapered surface of portion 304. The layer 326 can then be formed to cover at least that portion of the tapered surface which will receive this somewhat diverging laser light beam.

Light of any wavelength can be utilized in the device by selecting an appropriate high temperature melting point material to be deposited into and/or over the material of tip element 300 to form the laser light energy absorbing layer 326. For example, tungsten absorbs not only the visible portion of the electromagnetic spectrum but also the infra-red. Hence with tungsten as the chosen high temperature melting point material for layer 326 the disclosed device can be readily used with both visible and infra-red type laser sources, with commensurate choice of output, performance and utility. The key to success here is that all of the light energy conveyed via the body of tip element 300 to layer 326 is absorbed and converted to heat thereat.

In the absence of layer 326, the laser light beam internally incident on the smooth tapered surface of portion 304 will simply internally reflect and continue forward toward end surface 306. Layer 326 containing a high temperature melting point constituent, however, readily absorbs the incident laser light and converts its energy into heat. Consequently, the entire surface of tapered portion 304 which is covered by layer 326 (including end face 306), becomes heated solely by absorbing laser light energy received from optic cable 204. This heated surface 326 can be used by the surgeon to locally apply heat to body tissues for vaporization, cauterization or coagulation as desired. Because the laser light in this embodiment is not directly emitted onto body tissue to be absorbed thereby, this embodiment does not raise local tissue temperatures to the point at which the tissue material vaporizes very rapidly. For certain applications, this is highly desirable. Note that this embodiment allows a surgeon to utilize an existing laser energy source, to efficiently apply the energy provided thereby without any laser light emission, in a different manner to obtain commensurately different operational results.

There are described above various embodiments of the structure of an exemplary laser device tip element, with which energy from a laser energy source may be delivered precisely at selected locations at controlled rates. The described structure of each of these embodiments ensures significant reduction of Fresnel losses where the optic fiber meets the tip element, without the need for cumbersome and complicated cooling means. This facilitates the user's handling of the hand-held energy-delivering element. The different embodiments disclosed herein further provide a wide array of useful applications of a common basic geometry. Consequently, once surgeons become familiar with handling of the tapered tip element, they may, without serious modification of their operating techniques, obtain a variety of desired results by appropriate selection of one or more of the disclosed embodiments.

As noted earlier, there are a myriad of devices which instead of "laser" light utilize ultraviolet light (in the range 100 Å to 3500 Å), "visible" light (in the range 350 Å to 10,000 Å), or "infrared" light (in the range 10,000 Å to 1,000,000 Å). Fresnel losses can occur when light in any of these wavelength bands is transmitted across an interface between a light-transmitting region (either vacuum in space or the ambient atmosphere) and a light-transmitting element, e.g., the canopy of a high performance fighter aircraft, a display case in a jewelry store or a museum, an optical disc on which a recording is to be made by the application of a high powered laser beam, and numerous other light utilizing elements in optical devices generally. Clearly, with the great disparity in size between the very small end surface at the end of an optical fiber and the outside surface of a fighter aircraft canopy or a large pane of glass in a display case in a museum, corrèsponding physical modifications must of necessity be made to the ion, implantation apparatus. This, however, is perceived as merely a problem of scaling with the disclosed invention to suit specific needs. It is believed, therefore, that the above detailed description, taken with the cited drawing figures, fully discloses the invention which is limited solely by the claims appended hereto.

Reference to FIGS. 4A-4D makes it clear how the ions are applied to an apparently flat surface. Clearly, the principle is exactly the same even if the surface 308 were non-flat, e.g., spherical, conical, cylindrical, or some other irregular shape. The layer 340 typically is of a much smaller thickness than either the thickness of the substrate element 302 or the lateral dimensions thereof. Therefore, for applications involving curved surfaces, e.g., a lens, a fighter aircraft canopy or the like, patience and conventional care in applying the layer 340 uniformly and in applying ions 344 should result in highly uniform layers of non-abruptly varying concentration and non-abruptly varying refractive index as desired.

Among the materials believed to be particularly suitable for producing the described non-abruptly varying refractive index region at the surface of an optical substrate to be used with infrared light are: quartz, silicon, germanium, zinc sulfide and zinc selenide. These and other materials specifically suited for applications involving selected wavelengths of light may be chosen and applied by the described techniques at comparatively low expense and with consistent quality of the resulting structures.

In this disclosure, there are shown and described only the preferred embodiments of the invention, but, as aforementioned, it is to be understood that the invention is capable of use in various other combinations and environments and is capable of changes or modifications within the scope of the inventive concept as expressed herein.

What is claimed is:

1. An improved light-utilizing device, in which light is conveyed from a first element formed of a first material having a first refractive index into a second element formed of a second material having a second refractive index, the improvement comprising:
   a layer comprising a third material and having a non-abruptly varying refractive index intermediate the magnitudes of the first and second refractive indices, said layer being disposed to provide a light path between the first and second elements such that a light transmission therebetween does not encounter an abrupt change in refractive index.

2. The device according to claim 1, wherein:
   the third material comprises a selected constituent incorporated into a selected surface of one of the elements to a predetermined depth in a non-abruptly varying concentration, to thereby form a region of non-abruptly varying refractive index of a corresponding predetermined thickness thereat.

3. The device according to claim 1, wherein:
   said constituent is applied by an ion beam mixing process for said incorporation thereof into the selected surface.

4. The device according to claim 2, wherein:
   said constituent is applied by an ion beam enhanced deposition process for said incorporation thereof into the selected surface.

5. The device according to claim 3, wherein:
   said constituent comprises a ceramic material.

6. The device according to claim 4, wherein:
   said constituent comprises a ceramic material.

7. The device according to claim 2, wherein:
   said constituent is the same as one of said first and second materials.

8. The device according to claim 7, wherein:
   said first material is silica and said second material comprises one of YAG, sapphire, zirconia, quartz, silicon, germanium, zinc sulfide and zinc selenide.

9. The device according to claim 2, wherein:
   the predetermined thickness of the first layer is in the range 50 Å to 10,000 Å.

10. A device according to claim 1, further comprising:
    a source providing light in the wavelength range of 100 Å to 3500 Å.

11. The device according to claim 1, further comprising:
    a source providing light in the wavelength range 3500 Å to 10,000 Å.

12. The device according to claim 1, further comprising:
    a source providing light in the wavelength range 10,000 Å to 1,000,000 Å.

13. The device according to claim 1, further comprising:
    a source providing laser light.

14. A method for reducing Fresnel losses in a light-utilizing device in which light is conveyed from a first element formed of a first material having a first refractive index into a second element formed of a second material having a second refractive index, wherein the improvement comprises the step of:
    providing a first layer comprising a third material and having a non-abruptly varying refractive index intermediate the magnitudes of the first and second refractive indices, said first layer being disposed to provide a light path between the first and second elements such that a light transmission therebetween does not encounter an abrupt change in refractive index.

15. The method according to claim 14, wherein:
    the step of providing the first layer comprises the step of applying a selected constituent by ion beam mixing at a selected surface of one of the elements, to incorporate the constituent into the selected surface to a predetermined depth in a non-abruptly varying concentration.

16. The method according to claim 14, wherein:
    the step of providing the first layer comprises the step of applying a selected constituent by ion beam enhanced deposition at a selected surface of one of the elements, to incorporate the constituent into the selected surface to a predetermined depth in a non-abruptly varying concentration.

17. The method according to claim 15, wherein:
    said constituent is a ceramic material.

18. The method according to claim 16, wherein:
    said constituent is a ceramic material.

19. The method according to claim 16, comprising the further step of:
    applying more of said selected constituent to form a second layer thereof on said first layer.

20. A method for reducing Fresnel losses in a light-utilizing device in which light is provided from a first element formed of a first material having a first refractive index into a second element formed of a second material having a second refractive index, wherein the improvement comprises the step of:
    transmitting light through a third material having a non-abruptly varying refractive index of a magnitude intermediate the magnitudes of the first and second refractive indices, wherein said third refractive index continuously and non-abruptly varies from a value corresponding to that of the first refractive index of the first material to a value corresponding to that of the refractive index of the second material in a direction of transmission of the light.

21. An improved light-receiving element formed of a first material having a first refractive index and formed for receiving light within a selected waveband through a second material having a second refractive index, the improvement comprising:

a region of the element, at a light-receiving surface thereof, comprising a non-abruptly varying refractive index intermediate the magnitudes of the first and second refractive indices, said region being formed to a predetermined depth from the light-receiving surface and comprising a third material whereby the region provides a light path into the first material such that a light transmission through the region does not encounter an abrupt change in refractive index.

22. The element according to claim 21, wherein:
the third material comprises a selected constituent incorporated into said region through said light-receiving surface in a non-abruptly varying concentration to said predetermined depth.

23. The element according to claim 22, wherein:
said constituent is applied to said light-receiving surface by an ion beam mixing process for said incorporation thereof into the light-receiving surface.

24. The element according to claim 22, wherein:
said constituent is applied to said light-receiving surface by an ion beam enhanced deposition process for said incorporation thereof into the light-receiving surface.

25. The element according to claim 23, wherein:
said constituent comprises a ceramic material.

26. The element according to claim 24, wherein:
said constituent comprises a ceramic material.

27. The element according to claim 22, wherein:
the predetermined depth of the region is in the range 50 Å to 10,000 Å.

28. The element according to claim 27, wherein:
said third material is selected such that the region transmits light in the wavelength range 100 Å to 3500 Å.

29. The element according to claim 27, wherein:
said third material is selected such that the region transmits light in the wavelength range 3500 Å to 10,000 Å.

30. The element according to claim 27, wherein:
said third material is selected such that the region transmits light in the wavelength range 10,000 Å to 1,000,000 Å.

31. A method for reducing reflection of light received at a light-receiving surface to which light is conveyed from a first material having a first refractive index into an element formed of a second material having a second refractive index, wherein the improvement comprises the step of:

providing a layer comprising a third material and having a non-abruptly varying refractive index intermediate the magnitudes of the first and second refractive indices, said layer being formed in said second material to a predetermined depth and disposed to provide a light path between the first and second materials such that a light transmission therebetween does not encounter an abrupt change in refractive index.

32. The method according to claim 31, wherein:
the step of providing the layer comprises the step of applying a selected constituent by ion beam mixing into the light-receiving surface of one of the elements, to incorporate the constituent into the second material to a predetermined depth below the light-receiving in a non-abruptly varying concentration.

33. A method according to claim 31, wherein:
the step of providing the layer comprises the step of applying a selected constituent by ion beam enhanced deposition into the light-receiving surface of one of the elements, to incorporate the constituent into the second material to a predetermined depth below the light-receiving surface in a non-abruptly varying concentration.

34. The method according to claim 32, wherein:
said constituent is a ceramic material.

35. The method according to claim 33, wherein:
said constituent is a ceramic material.

36. A method for reducing reflection losses at a light-receiving surface to which light in a selected waveband is provided through a first material having a first refractive index into a second material having a second refractive index, wherein the improvement comprises the step of:

transmitting light through a third material having a non-abruptly varying refractive index of a magnitude intermediate the magnitudes of the first and second refractive indices, wherein said third refractive index continuously and non-abruptly varies from a value corresponding to that of the first refractive index of the first material to a value corresponding to that of the refractive index of the second material in a direction of transmission of the light.

37. A method for forming an improved efficient infrared-transmissive system having an infrared-receiving surface to which infrared radiation is conveyed from a first material having a first refractive index into an element formed of a second material having a second refractive index, wherein the improvement comprises the step of:

providing a first layer comprising a third material and having a non-abruptly varying refractive index intermediate the magnitudes of the first and second refractive indices, said first layer being formed in said second material to a predetermined depth and disposed to provide a light path between the first and second materials such that a light transmission therebetween encounters a non-abrupt change in refractive index, wherein said second material comprises one of quartz, silicon, germanium, zinc sulfide and zinc selenide.

38. The method according to claim 37, wherein:
the step of providing the first layer comprises the step of applying a selected constituent by ion beam mixing at said surface of the element, to incorporate the constituent into the surface to a predetermined depth in a non-abruptly varying concentration.

39. The method according to claim 37, wherein:
the step of providing the first layer comprises the step of applying a selected constituent by ion beam enhanced deposition to said surface of the element, to incorporate the constituent into the surface to a predetermined depth in a non-abruptly varying concentration.

40. The method according to claim 39, comprising the further step of:
applying more of said selected constituent to form a second layer thereof on said first layer.

* * * * *